(12) United States Patent
Cancel et al.

(10) Patent No.: US 7,217,238 B2
(45) Date of Patent: May 15, 2007

(54) IMPLANTABLE PROSTHESIS FOR CORRECTING URINARY STRESS INCONTINENCE IN WOMEN

(75) Inventors: Richard Cancel, La Garde (FR);
Richard Wallace, Gonfaron (FR);
Gerard Sassi, Toulon (FR)

(73) Assignee: Europlak (FR)

( * ) Notice: Subject to any disclaimer, the term of this patent is extended or adjusted under 35 U.S.C. 154(b) by 251 days.

(21) Appl. No.: 10/889,562

(22) Filed: Jul. 12, 2004

(65) Prior Publication Data

US 2005/0000524 A1    Jan. 6, 2005

Related U.S. Application Data

(63) Continuation of application No. PCT/FR03/00105, filed on Jan. 14, 2003.

(30) Foreign Application Priority Data

Jan. 14, 2002    (FR) ................................. 02 00385

(51) Int. Cl.
*A61F 2/02* (2006.01)

(52) U.S. Cl. ...................................................... 600/30

(58) Field of Classification Search ............ 600/29–31; 128/885, DIG. 25; 607/138; 606/139, 151
See application file for complete search history.

(56) References Cited

U.S. PATENT DOCUMENTS

| 5,591,163 A | 1/1997 | Thompson |
| 5,647,836 A | 7/1997 | Blake, III et al. |
| 6,068,591 A | 5/2000 | Bruckner et al. |
| 2002/0128670 A1* | 9/2002 | Ulmsten et al. ............ 606/151 |

FOREIGN PATENT DOCUMENTS

| EP | 0 632 999 A1 | 1/1995 |
| FR | 2 785 521 A1 | 5/2000 |
| FR | 2 787 990 A1 | 7/2000 |
| WO | WO 02/02031 A1 | 1/2002 |

* cited by examiner

*Primary Examiner*—John P. Lacyk
(74) *Attorney, Agent, or Firm*—DLA Piper US LLP

(57) ABSTRACT

A prosthesis for correcting urinary stress incontinence in women including right and left para-urethral hemi-prostheses, each of the hemi-prostheses formed of a biocompatible material and in the form of a strip, one end of the strip having a bulged portion and another end of which is adapted to be attached to the aponeurosis of the rectus muscle of the abdomen, and means for attaching the another end to the aponeurosis of the rectus muscle of the abdomen.

18 Claims, 2 Drawing Sheets

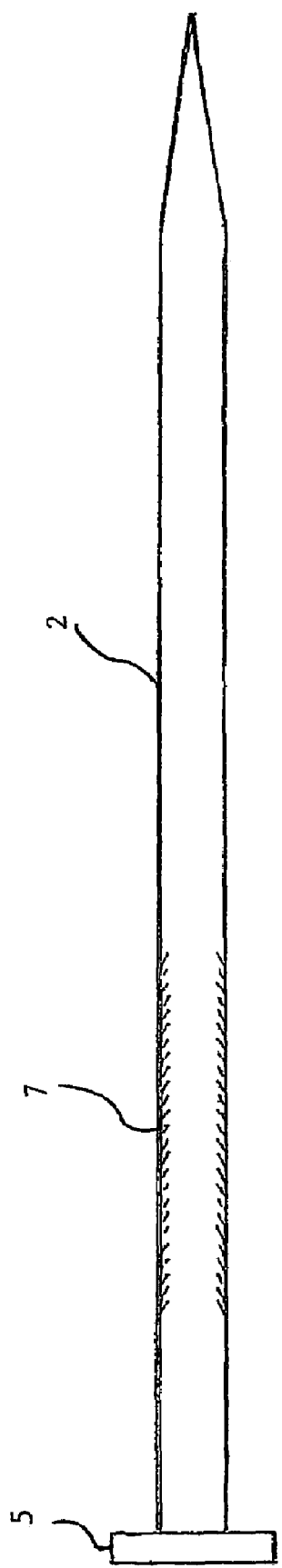
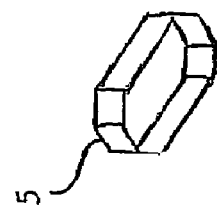
Figure 2
Figure 3

IMPLANTABLE PROSTHESIS FOR CORRECTING URINARY STRESS INCONTINENCE IN WOMEN

RELATED APPLICATION

This is a continuation of International Application No. PCT/FR03/00105, with an international filing date of Jan. 14, 2003 (WO 03/057074, published Jul. 17, 2003), which is based on French Patent Application No. 02/00385, filed Jan. 14, 2002.

FIELD OF THE INVENTION

This invention relates to a prosthesis for correcting urinary stress incontinence in women.

BACKGROUND

Urinary stress incontinence is a pathology occurring most often after obstetric trauma. The ligaments supporting the bladder often become distended and the bladder is pushed downwardly and out of the pelvic cavity which normally supports it. The angle of the bladder at the level of the bladder neck is opened and—upon an effort such as sneezing—the urethra, which is no longer protected by the pelvic cavity, is subjected to the totality of the pressure generated by the stress and an incontinence phenomenon occurs.

This phenomenon has been well known and various solutions have been attempted. WO 00/15140 discloses an intra-urethral prosthesis. EP-A-498912 discloses a sub-urethral prosthesis designed to be implanted for a limited period of time at the level of the vagina. FR-A-2787990 discloses a prosthesis constituted of two right and left hemi-prostheses, each hemi-prosthesis comprising a net attached to the vaginal wall on which is anchored a thread the other end of which is attached to the base of the rectus muscle of the abdomen. The net is a sub-urethral element on which the bladder neck rests.

The prostheses of the prior art represent a certain number of risks for the patient, notably the risk of tearing of the bladder or damage caused to the bladder neck or the urethra when the prosthesis is installed. Sub-urethral materials also have drawbacks in use by preventing or restricting miction.

SUMMARY OF THE INVENTION

This invention relates to a prosthesis for correcting urinary stress incontinence in women including right and left para-urethral hemi-prostheses, each of the hemi-prostheses formed of a biocompatible material and in the form of a strip, one end of the strip having a bulged portion and another end of which is adapted to be attached to the aponeurosis of the rectus muscle of the abdomen, and means for attaching the another end to the aponeurosis of the rectus muscle of the abdomen.

BRIEF DESCRIPTION OF THE DRAWINGS

Other characteristics and advantages of the prosthesis according to the invention will become clear from the nonlimitative example of implementation below which is presented with reference to the attached figures:

FIG. 2 is a top view of one of the constitutive hemi-prostheses of a prosthesis according to aspects of the invention comprising reverse lock notches hollowed out in the constitutive material of the strip; and FIG. 3 shows a detail of FIGS. 1 and 2, i.e., the bulge (5).

DETAILED DESCRIPTION

Figure 1:
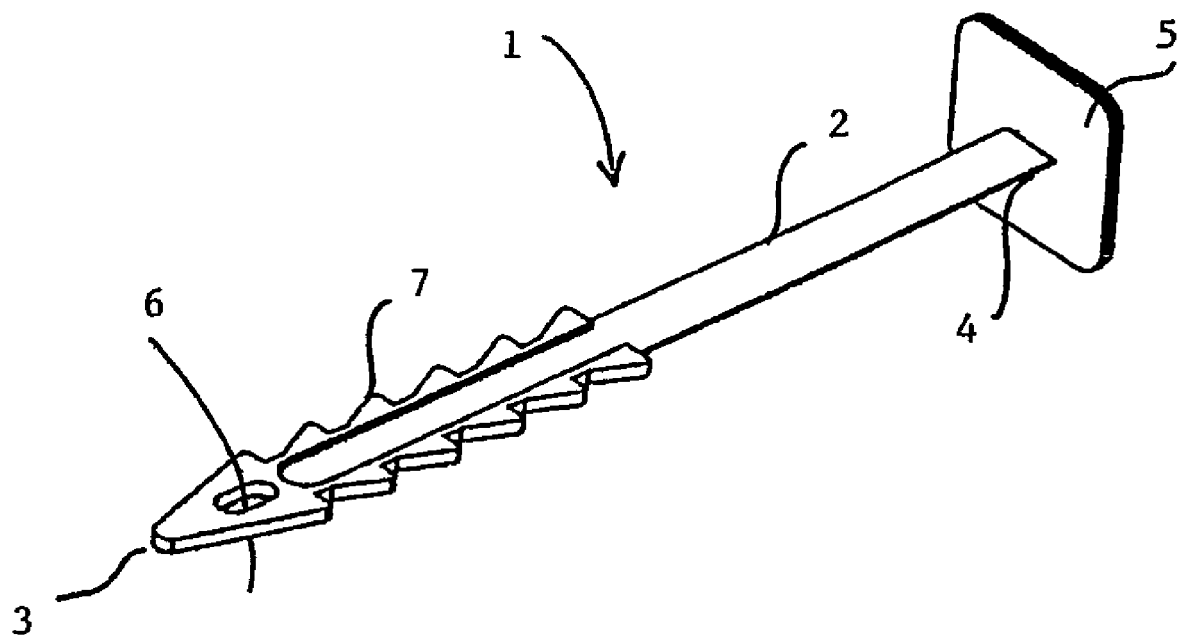
FIG. 1 is a top perspective view of one of the two hemi-prostheses constituting a prosthesis in accordance with aspects of the invention bearing overmolded reverse lock notches.

It will be appreciated that the following description is intended to refer to specific embodiments of the invention selected for illustration in the drawings and is not intended to define or limit the invention, other than in the appended claim.

This invention can provide a prosthesis that can be installed definitively by a simple surgical operation without substantial risk of damaging organs and, notably, without substantial risk of tearing the bladder or the urethra. The invention can also provide a prosthesis that corrects the hypermobility of the urethra upon effort. It is this hypermobility that leads to an incontinence phenomenon. The invention can further assist in maintaining the natural angle at the level of the bladder neck.

The invention thus provides a prosthesis for correcting urinary stress incontinence in women comprising right and left para-urethral hemi-prostheses, each of the hemi-prostheses comprising a biocompatible material and formed of a strip one end of which has a bulge and the other end of which, referred to as the "free end," is intended to be attached to the aponeurosis of the rectus muscle of the abdomen, and means for attaching the free end to the aponeurosis of the rectus muscle of the abdomen.

According to one aspect, the bulge is a pad made integral with one of the two ends of each strip. When the prosthesis is in position, the bulges or pads are supported on the subject's perineal muscle-aponeurosis floor on either side of the urethra and the strips are situated in the Retzius's space in front of the bladder, traversing the abdominal wall above the pubic symphysis and are attached to the aponeurosis of the rectus muscle of the abdomen.

The prosthesis according to the invention does not require a sub-urethral device.

The strips and the pads are manufactured of a material acceptable for long-term implants. The material is preferably polypropylene (PP) of a grade acceptable for implants intended to remain in place in the human body for an indefinite period of time. According to one aspect, the section of each of the strips is between about 1 and about 15 mm, preferably about 4 to about 10 mm, and is advantageously equal to about 6.5 mm.

According to a preferred aspect, the length of the strips not including the bulge is about 100 to about 300 mm, preferably about 170 to about 270 mm, and is advantageously equal to about 210 to about 220 mm. The length of the bulge is preferably about 10 to about 30 mm, preferably about 20 mm, and the section of the bulge is about 5 to about 20 mm, preferably about 10 mm. The bulge is preferably of octagonal shape.

According to another aspect, the strips comprise reverse lock notches preferably made of a material acceptable for the manufacture of long-term implants. The material is preferably silicone of a grade acceptable for implants intended to remain in the human body for an indefinite period of time. The reverse lock notches may be overmolded over all or part of each strip. The notches are preferably overmolded over a length of about 30 to about 80 mm, preferably about 60 mm, at a distance of about 10 to about 50 mm, preferably about 30 mm, in relation to the end of the strip comprising a bulge. The reverse lock notch is overmolded above the body of the strip. Therefore, the section of the strip and the reverse lock notches taken together is, at the overmolding location, greater than the section of the strip without notches. The section of the strip and the reverse lock notches taken together are preferably about 3 to about 20 mm, preferably about 5 to about 15 mm, and advantageously equal to about 11 mm.

According to another aspect, the strips are fitted with reverse lock notches hollowed or cut out manually or mechanically in the constitutive material of the strip. The reverse lock notches are preferably hollowed out at a distance of abut 10 to about 40 mm, preferably about 30 mm, from the base of the pad. They are advantageously distributed over a length of about 30 to about 70 mm, preferably about 50 mm.

According to another aspect, the strip is molded in a recess mold. The recesses preferably open the strips circularly. Preferably, the recesses are separated from each other by a space of about 2 mm.

According to yet another aspect, a propylene thread is welded between the two polypropylene strips and the means for attaching the strips to the aponeurosis of the rectus muscle of the abdomen are threads. In this aspect, the free end of the strip is integral with an attachment thread. This attachment thread may be used for implantation of the prosthesis by a needle through the eye of which the attachment thread is passed. Advancing the needle into the Retzius's space results in implantation of the suture of the strip on the aponeurosis of the rectus muscle of the abdomen. The attachment means may also be means for gluing the strips. The attachment means may further be static-based self-adhesive means.

The right and left hemi-prostheses are substantially identical and FIGS. 1 and 2 each show one of the two hemi-prostheses comprising the prosthesis of the invention. The hemi-prostheses (1) are each formed of a strip (2), one end (3) of which, referred to as the "free end," is intended to be attached to the aponeurosis of the rectus muscle of the abdomen and the other end (4) of which has a pad (5) intended to be positioned in a para-urethral receptacle created during the surgical intervention.

The strip (2) may be of sufficient length to traverse the Retzius's space from the aponeurosis of the rectus muscle of the abdomen to the urethra. Not counting the pad (5), the length of the strip (2) is preferably about 100 to about 300 mm. After completion of installation, the strip (2) is under tension.

The function of the strip (2) is to maintain the pad (5) in place: it is an anchoring band. It also has a traction function due to the fact of being installed under tension. It is the combination of these functions of attachment and traction which hold the hemi-prosthesis in place and provide its efficacy. The strip (2) also has silicone reverse lock notches overmolded on the polypropylene strip and reinforce holding the strip in place. Moreover, over time, the non-overmolded parts of the polypropylene strip (2) will be colonized by cells in the human body and this colonization will further reinforce holding the strip in place.

FIG. 1 shows a strip fitted with reverse lock notches (7) overmolded on the strip. These reverse lock notches (7) have a mechanical function of retaining the strip close to the pad. FIG. 2 shows a strip fitted with reverse lock notches (7) cut into the strip or created in the strip during molding by a special mold comprising corresponding lugs. These reverse lock notches have the same mechanical function of retaining the strip close to the pad.

FIG. 3 shows a bulge (5) which is a pad that can be made of the same material as the strip or of another biocompatible material for long-term implants. It can be cast at the same time as the strip (2) or separately. In the case of separate molding, it is made integral with the strip (2) by any suitable means, notably by welding. This pad (5) has the function notably of preventing the hypermobility of the urethra precisely at the time of effort. Its elongated octagonal form is preferred.

The installation of each hemi-prosthesis (1) requires a simple surgical intervention, during which a sub-urethral longitudinal incision is made. A separation is then effected to create a para-urethral receptacle at the right and left up to the pelvic aponeurosis. It is in this receptacle that will come to be positioned the bulge located at the end of each hemi-prosthesis.

A cutaneous incision to the left and right of the pubic symphysis is preformed and extended to the aponeurosis of the rectus muscle of the abdomen to penetrate the Retzius's space. For installation of each hemi-prosthesis (1), one uses a needle through which is threaded a thread (6) connected to the free end (3) of the strip (2). The needle is passed into the Retzius's space while maintaining osseous contact and enabling installation of the strip (2). The vaginal incision is closed with resorbable threads. The efficacy of the tension of the strip (2) is then adjusted and tested. The bladder is filled with 300 cc of physiological serum and pressure is applied to the bladder until the tension of the strip (2) prevents passage of the liquid. The free end (3) of the strip (2) is then attached to the aponeurosis of the rectus muscle of the abdomen by a suture.

The prosthesis of the invention can thus be easily installed and requires only a simple surgical intervention.

The invention claimed is:

1. A prosthesis for correcting urinary stress incontinence in women comprising right and left para-urethral hemi-prostheses, each of the hemi-prostheses comprising:
   a biocompatible material strip, one end of the strip having a bulged portion and another end shaped for attachment to the aponeurosis of the rectus muscle of the abdomen, and
   means for attaching the another end to the aponeurosis of the rectus muscle of the abdomen, wherein the strip is an anchoring band that maintains the bulged portion in a selected position.

2. The prosthesis according to claim 1, wherein the bulged portion is a pad integral with one of the ends of the strip.

3. The prosthesis according to claim 1, wherein the strip is of sufficient length to traverse the Retzius's space from the aponeurosis of the rectus muscle of the abdomen to the urethra.

4. The prosthesis according to claim 1, wherein the strip and the bulge are made of a material acceptable for long-term implants.

5. The prosthesis according to claim 4, wherein the material is polypropylene.

6. The prosthesis according to claim 1, wherein the strip comprises reverse lock notches.

7. The prosthesis according to claim 6, wherein the reverse lock notches are made of a material acceptable for long-term implants.

8. The prosthesis according to claim 7, wherein the material is silicone of a grade acceptable for implants intended to remain in place in the human body for an indefinite period of time.

9. The prosthesis according to claim 1, wherein the strip has a cross section of about 1 to about 15 mm.

10. The prosthesis according to claim 1, wherein the length of the strip, not including the bulge, is between about 100 and about 300 mm.

11. The prosthesis according to claim 6, wherein the reverse lock notches are overmolded over all or part of the strip.

12. The prosthesis according to claim 9, wherein the cross section of the strip and the reverse lock notches on the strip taken together is between about 3 and about 20 mm.

13. The prosthesis according to claim 6, wherein the reverse lock notches are hollowed out of a surface of the strip.

14. The prosthesis according to claim 6, wherein the reverse lock notches are created over a length of about 30 to about 80 mm, at a distance of 10 to 50 mm in relation to the another end of the strip.

15. The prosthesis according to claim 1, wherein the length of the bulge is between about 10 and about 30 mm and the cross section of the bulge is between about 5 and about 20 mm.

16. The prosthesis according to claim 1, wherein the means for attachment is a thread.

17. The prosthesis according to claim 1, wherein the means for attachment are means for gluing.

18. The prosthesis according to claim 1, wherein the means for attachment are static-based self-adhesive means.

\* \* \* \* \*